United States Patent [19]

Myers et al.

[11] Patent Number: 4,912,094

[45] Date of Patent: Mar. 27, 1990

[54] MODIFIED LIPOPOLYSACCHARIDES AND PROCESS OF PREPARATION

[75] Inventors: Kent R. Myers; Alex T. Truchot, both of Hamilton, Mont.

[73] Assignee: Ribi ImmunoChem Research, Inc., Hamilton, Mont.

[21] Appl. No.: 212,919

[22] Filed: Jun. 29, 1988

[51] Int. Cl.$^4$ .................. C07H 1/00; C07H 13/02; C07G 17/00; C12P 19/04
[52] U.S. Cl. ...................................... 514/54; 536/124; 536/1.1; 536/119; 536/117; 536/115; 435/101
[58] Field of Search ............... 536/124, 1.1, 119, 115, 536/117; 435/101; 514/54

[56] References Cited

U.S. PATENT DOCUMENTS

| | | | |
|---|---|---|---|
| 3,089,821 | 5/1963 | Folkers | 514/54 |
| 4,029,762 | 6/1977 | Galanos et al. | 530/387 |
| 4,185,090 | 1/1980 | McIntire | 536/1.1 |

*Primary Examiner*—Ronald W. Griffin
*Assistant Examiner*—Everett White
*Attorney, Agent, or Firm*—Burgess, Ryan and Wayne

[57] ABSTRACT

Modified lipopolysaccharides, particularly de-3-0-acylated monophosphoryl lipid A and de-3-0-acylated diphosphoryl lipid A, are provided by an alkaline hydrolysis under controlled conditions which removes only the $\beta$-hydroxymyristic acyl residue that is ester-linked to the reducing-end glucosamine at position 3. The modified products are less endotoxic and maintain their antigenic and immuno-stimulating properties.

26 Claims, No Drawings

MODIFIED LIPOPOLYSACCHARIDES AND PROCESS OF PREPARATION

FIELD OF THE INVENTION

This invention relates in general to certain modified forms of lipopolysaccharide and lipid A. In one aspect, this invention is directed to a process for the structural modification of certain lipopolysaccharides to render them less endotoxic without adversely affecting their antigenic or immuno-stimulating properties.

BACKGROUND OF THE INVENTION

Prior to the present invention, it had long been recognized that enterobacterial lipopolysaccharides (LPS) was a highly potent stimulator of the immune system. A variety of responses, both beneficial and harmful, can be elicited by sub-microgram amounts of this substance. The fact that some of these responses are harmful, and can in fact be fatal, has to date precluded clinical use of LPS per se. It is now also well-appreciated that the endotoxic activites associated with bacterial lipopolysaccharides (LPS) reside in the lipid A component of LPS.

Accordingly, much effort has been expended towards attenuating the toxic attributes of lipid A and LPS without diminishing their beneficial immunostimulatory activities. Notable among these efforts was that of Edgar Ribi and his associates, which resulted in the production of a derivative of lipid A referred to originally as refined detoxified endotoxin (RDE) but more recently as monophosphoryl lipid A (MPL). MPL is produced by refluxing LPS (or lipid A) obtained from heptoseless mutants of gram negative bacteria (e.g. Salmonella sp.) in mineral acid solutions of moderate strength (e.g., 0.1N HCl) for a period of approximately 30 minutes. This treatment results in the loss of the phosphate moiety at position 1 of the reducing-end glucosamine. Coincidentally, the core carbohydrate is removed from the 6' position of the non-reducing glucosamine during this treatment. The result is the monophosphoryl derivative of lipid A, MPL. The structure of MPL is shown below:

MPL exhibits considerably attenuated levels of the endotoxic activities normally associated with lipid A and LPS, such as pyrogenicity, local Shwarzman reactivity, and toxicity in the chick embryo 50% lethal dose assay ($CELD_{50}$). It retains the ability of lipid A and LPS, however, and to, among other things, act as an adjuvant.

The difficulty with this method of detoxifying LPS and lipid A is that it invariably results in the loss of the core moiety attached to position 6' of the non-reducing glucosamine. This is significant since the core region is highly conserved among LPS's obtained from different genera of Enterobacteriaciae; immunity against the core region is therefore protective against a wide variety of gram negative bacterial challenges. This was demonstrated by the work of Ziegler et al. (New Eng. J. Med. 307, 1225: 1982), for example.

Considerable benefits would accrue from being able to immunize individuals against enterobacterial LPS, as evidenced by the fact that approximately 90,000 deaths occur annually from gram negative sepsis and associated endotoxemia. At the present time, however, it is only possible to immunize with fully toxic LPS, since detoxification by acid hydrolysis results in loss of the core region.

Alkaline hydrolysis has also been used in the past to detoxify LPS, but the conditions which have generally been used result in complete saponification of the lipid A moiety. This, of course, not only reduces the endotoxicity of the starting LPS, but also eliminates the other, more beneficial, activities as well. Furthermore, such treatment also reduces the immunogenicity of LPS, since it is essentially converted by this treatment into a polysaccharide antigen with no amphipathic character. In general, however, none of the early references teach that removal of one particular fatty acid from lipid A would render it non-toxic, while not affecting its immunostimulating activities.

Accordingly, one or more of the following objects will be achieved by the practice of this invention. It is an object of this invention to provide modified lipopolysaccharrides and, in particular, modified lipid A. Another object of this invention is to provide a modified lipid A which retains the core moiety attached to the 6' positions of non-reducing glucosamine. A further object

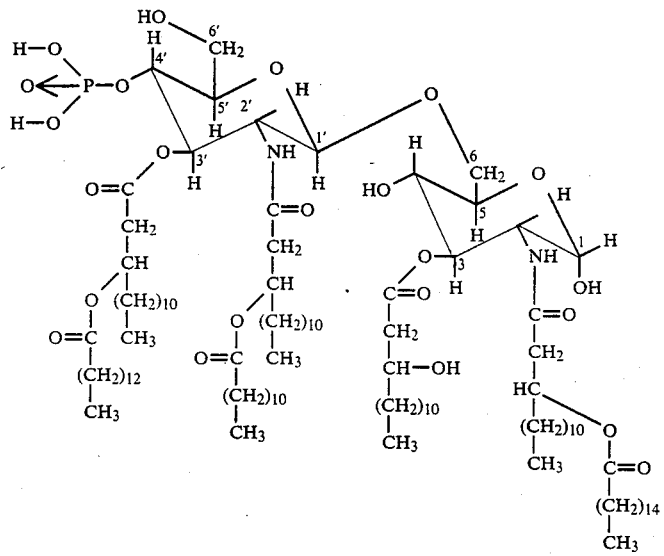

(I)

of the present invention is to provide a modified lipid A which retains the core moiety and accordingly, protection against a wide variety of gram negative challenges. A still further object of the present invention is to provide a process for the preparation of the modified lipid A which renders it less endotoxic without adversely affecting their antigenic or immunostimulating properties. Another object is to provide pharmaceutical compositions containing the modified lipopolysaccharides and a method for their use. These and other objects will readily become apparent to those skilled in the art in light of the teachings herein set forth.

SUMMARY OF THE INVENTION

In its broad aspect, the present invention is directed to certain modified forms of lipopolysaccharide and lipid A, and to a process for their preparation. The invention also encompasses pharmaceutical compositions containing the modified lipopolysaccharides and their use in the treatment of various conditions in warm blooded animals.

The modified lipopolysaccharides and lipid A of this invention are those which have been subjected to a mild alkaline hydrolysis under conditions as hereinafter defined that result in the loss of a single fatty acid from position 3 of the lipid A backbone.

DETAILED DESCRIPTION OF THE INVENTION

There is a considerable body of literature which pertains to the effect of alkaline treatment on the biological activities of LPS and lipid A. Most of these references teach the use of conditions that are sufficient to completely deacylate lipid A. As stated earlier, such treatment destroys essentially all biological activity of lipid A and LPS, except for antigenicity. The early paper by Neter et al. (Neter E., Westpahl O., Luderitz O., Gorzynski E. A. and Eichenberger E., "Studies of enterobacterial lipopolysaccharides". Effects of heat and chemicals on erythrocyte modifying, antigenic, toxic, and pyrogenic properties", J. Immunol. 76, 377: 1956), can be regarded as representative of the state of the art which teach the use of alkaline conditions sufficient to destroy all biological activities of LPS.

Several other observations have been noted in the scientific literature concerning alkaline hydrolysis of lipid A and LPS. For example, Niwa et al. (J. Bacterial. 97, 1069: 1969;) observed that treatment of LPS with mildly alkaline conditions caused a rapid loss of endotoxic activity and a much slower loss of fatty acids. This observation led them to conclude that the fatty acid-containing portion of LPS, lipid A, was not responsible for the endotoxic activity of LPS, since it was evidently destroyed at a slower rate than the endotoxic activity was lost. The authors conjectured that the only way that their observations might be consistent with lipid A being the endotoxic principle was if there existed a fatty acid in lipid A that was both highly alkaline-labile and necessary for endotoxic activity. The authors did not consider this to be a likely explanation. At the time, Niwa et al. favored an explanation for their results based on the influence of mild alkaline treatment on the conformation of endotoxin aggregates.

In a paper by Rietschel et al. (Eur. J. Biochem. 28, 166; 1973), it was noted that $\beta$-hydroxymyristic acid is rapidly released from lipid A upon mild alkali treatment (0.25N NaOH, 56° C.). The reason for the rapid loss of $\beta$-hydroxymyristic acid was not given, nor was it known from which position this fatty acid was cleaved. Also, no mention was made of the relationship of this rapid loss of $\beta$-hydroxymyristic acid to the loss of endotoxicity upon mild alkaline treatment which was observed by Niwa et al. and others.

In a paper by Goodman and Sultzer (Infect. Immunity 17, 205: 1977;) the authors noted that mild alkaline hydrolysis of LPS reduced its toxicity while actually enhancing its mitogenicity. They chemically characterized the hydrolyzed product with respect to nitrogen, glucosamine, KDO, and fatty acid content. Significantly, they found that the fatty acid content was relatively unchanged by the alkaline treatment. This led Goodman and Sultzer to conclude that the effect of the mild alkaline treatment was mediated by changes in the aggregational properties of the hydrolyzed LPS. In this regard, they were adopting the view of Niwa et al. On p. 212 of their paper, Goodman and Sultzer state that " . . . we have reduced the toxicity of the [LPS] by about 100-fold without significantly changing the lipid moiety." This confirms that they did not understand what they had done to achieve the observed reduction in toxicity without reducing mitogenicity. No mention was made of the possibility of a critical fatty acid that is alkaline-labile.

The sensitivity of ester-linked $\beta$-hydroxymyristic fatty acid residues present in lipid A to alkaline hydrolysis was noted in a 1982 publication (N. Qureshi, D. Takayama, and E. Ribi, J. Biol. Chem. 257, 11808: 1982). Similar observations were made with respect to a monosaccharide precursor of lipid A in a 1983 publication (Takayama, et al., J. Biol. Chem 258, 14245: 1983). Both of these references teach that ester-linked $\beta$-hydroxymyristic fatty acid residues present in lipid A or related compounds are easily removed by mild alkaline treatment. The effect of this structural modification on the biological activity of lipid A was not recognized in this or any subsequent references.

The treatment of LPS with mild alkali was discussed in two papers by Amano, et al. (D. Amano, E. Ribi, and J. L. Cantrell, J. Biochem 93, 1391: 1983, and K. Amano, E. Ribi, and J. L. Cantrell, BBRC 106, 677: 1982). The authors reported that mild alkali treatment results in the loss of O-ester linked fatty acids. They did not mention that the only fatty acid removed by this treatment is the $\beta$-hydroxymyristic at position 3. Also, contrary to the results disclosed in the present invention, they reported that mild alkali treatment did not reduce the endotoxicity of the parent LPS.

A study of the structural consequences of treating LPS with mild alkali was reported in a paper by Rosner, et al. (M. R. Rosner, J-y Tang, I. Barzilay, and H. G. Khorana, J. Biol. Chem 254, 5906: 1979). The authors reported that LPS which was treated with 1N NaOH at room temperature for approximately 17 hrs was exhaustively de-O-acylated. This is clearly different from the present invention, which discloses conditions sufficient to remove only the $\beta$-hydroxymyristic from position 3. Furthermore, the authors subjected LPS to this mild alkali treatment solely for the purpose of elucidating LPS's structure. No mention is made in this article of the effect of mild alkali treatment on the biological activities of LPS.

The use of mild alkali treatment to lower the toxicity of lipid A was disclosed in U.S. Pat. No. 4,029,762. this patent discloses the use of lipid A and alkali-treated lipid A as antigens for stimulating immunity against gram-negative enterobaceriaceae. It was not disclosed in this patent that lipid A, which lacked a β-hydroxymyristic acid at position 3, is less endotoxic but is still mitogenic.

In a 1987 review by Rietschel et al. (in "Detection of Bacterial Endotoxins with the Limulus Amebocyte Lysate Test", Alan R. Liss, Inc., 1987, p. 25–53;), mention is made of the fact that synthetic monosaccharides corresponding to the reducing end of lipid A are inactive if the β-hydroxymyristic acid residue at position 3 is removed. The authors, however, did not conjecture as to whether the same observation would be made with lipid A, and no work was cited pertaining to this question. It does not appear then that it was suspected that removal of the β-hydroxymyristic acid from position 3 of lipid A and LPS would result in reduced endotoxicity without affecting activities such as mitogenicity.

Accordingly, prior to the present invention, and in view of the reported research efforts of Edgar Ribi and his colleagues, in preparing and evaluating monophosphoryl lipid A, it was generally recognized that detoxification of lipopolysaccharide was best accomplished by an acid hydrolysis followed by a chromatographic separation of MPL if a product having enhanced immuno-stimulating properties was desired. It was not readily apparent that the endotoxicity of lipid A could be attenuated by removal of only the fatty acid at position 3 or that removal of the position 3 fatty acid from lipopolysaccharide would reduce endotoxicity and yet allow other desirable substituents to remain in the molecule.

Thus, in contrast to the prior art references which may disclose, in general, the alkaline treatment of lipopolysaccharides, none of these references clearly recognizes the unexpected and surprising results obtained by employing conditions for removal of only the β-hydroxymyristic acyl residue from lipopolysaccharides and thereafter separating and recovering the deacylated product in a relatively pure form.

Lipid A deacylated in accordance with the method of the present invention was found to be non-toxic in the $CELD_{50}$ assay ($CELD_{50} > 10$ μg), in spite of the fact that it still contained (1) a diglucosamine backbone, (2) two phosphoryl groups, (3) at least two 3-acyloxyacyl residues, and (4) up to a total of 6 fatty acids. Taken together, these results indicate that the total number of fatty acids present in lipid A is not a sufficient condition for the manifestation of endotoxic activity, but that the pattern of fatty acid substitution is also a critical determinant.

While not wishing to be bound by any theory regarding the reasons why the compound(s), although less endotoxic, are still able to exert a strong immunostimulating effect, it is believed that the specific structural modification that is responsible for this reduction in the endotoxicity of lipid A and LPS involves removing of the β-hydroxymyristic acyl residue that is ester-linked to the reducing-end glucosamine at position 3 under conditions which do not adversely affect other groups in the lipopolysaccharides. Monophosphoryl lipid A (MPL), diphosphoryl lipid A (DPL) and LPS can all be de-3-O-acylated in this way. The structures of these novel materials are shown below in formula II wherein the figures in the circles indicates the number of carbon atoms in the chain.

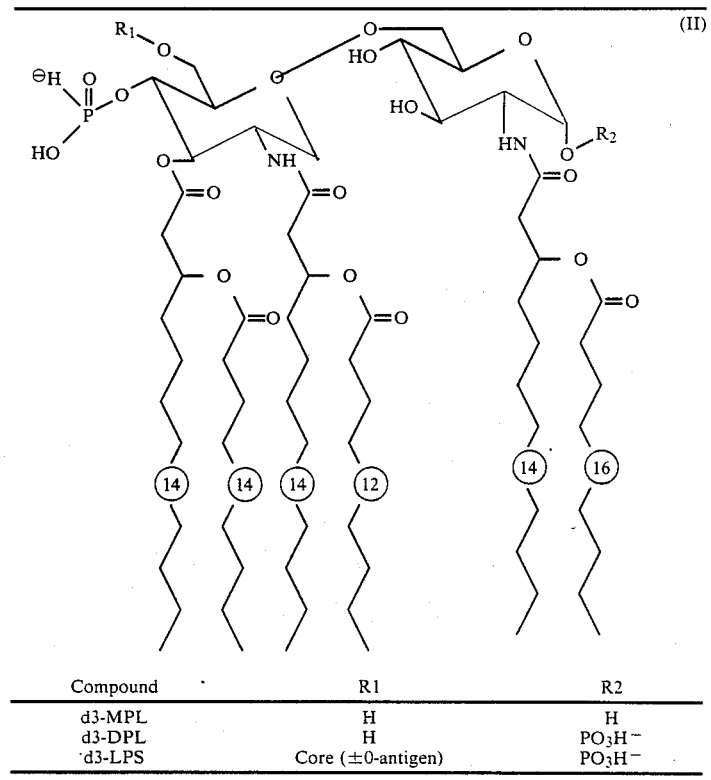

| Compound | R1 | R2 |
|---|---|---|
| d3-MPL | H | H |
| d3-DPL | H | $PO_3H^-$ |
| d3-LPS | Core (±0-antigen) | $PO_3H^-$ |

Various forms of de-3-O-acylated materials are encompassed by this invention. The lipid A backbone that is shown corresponds to the product that is obtained by de-3-O-acylation of heptaacyl lipid A from *S. minnesota* R595. Other fatty acid substitution patterns are encompassed by this disclosure; the essential feature is that the material be de-3-O-acylated.

Thus, one embodiment of this invention is directed to the composition of MPL, DPL and LPS in which the position 3 of the reducing end glucosamine is de-O-acylated. These compounds as indicated above are referred to as d3-MPL, d3-DPL, and d3-LPS, respectively.

Also as indicated above, the modified lipopolysaccharides of the present invention are prepared by subjecting the compounds to alkaline hydrolysis under conditions that result in the loss of but a single fatty acid from position 3 of the lipid A backbone.

The $\beta$-hydroxymyristic at position 3 is unusually labile in alkaline media. It requires only very mild alkaline treatment to completely de-3-O-acylate lipid A and LPS. The other ester linkages in lipid A and LPS require somewhat stronger conditions before hydrolysis will occur, so that it is possible to selectively deacylate these materials at position 3 without significantly affecting the rest of the molecule. The reason for the unusual sensitivity to alkaline media of the ester-linked $\beta$-hydroxymyristic at position 3 is not known at this time.

Although alkaline hydrolysis procedures are known, it is important to choose conditions that do not cause further hydrolysis beyond the ester linkage to the $\beta$-hydroxymyristic at position 3.

In general, the hydrolysis can be carried out in aqueous or organic media. In the latter case, solvents include methanol (alcohols), dimethyl sulfoxide (DMSO), dimethylformanide (DMF), chloroform, dichloromethane, and the like as well as mixtures thereof. Combinations of water and one or more of these organic solvents also can be employed.

The alkaline base can be chosen from among various hydroxides, carbonates, phosphates and amines. Illustrative bases include the inorganic bases such as sodium hydroxide, potassium hydroxide, sodium carbonate, potassium carbonate, sodium bicarbonate, potassium bicarbonate, and the like, and organic bases such alkyl amines and include, but are not limited to, diethylamine, triethylamine and the like.

In aqueous media, the pH is typically between approximately 10 and 14 with a pH of about 12 to about 13.5 being the preferred range. The hydrolysis reaction is typically carried out at a temperature of from about 20° to about 80° C., preferably about 50° to about 60° C. for a period of about 10 to about 30 min. For example, the hydrolysis can be conducted in 3% triethylamine in water at room temperature (22°–25° C.) for a period of 48 hrs. The only requirement in the choice of temperature and time of hydrolysis is that de-O-acylation occurs to remove only the $\beta$-hydroxymyristic at position 3.

In practice, it has been found that a particularly desirable hydrolysis method involves dissolving liquid A or monophosphoryl lipid A in chloroform:methanol 2:1 (v/v), saturating this solution with an aqueous buffer consisting of 0.5M $Na_2CO_3$ at pH 10.5, and then to flash evaporate the solvent at 45°–50° C. under a vacuum for an aspirator (approximately 100 mm Hg). The resulting material is selectively deacylated at position 3. This process can also be carried out with any of the inorganic bases listed above. The addition of a phase transfer catalyst, such as tetrabutyl ammonium bromide, to the organic solution prior to saturating with the aqueous buffer may be desirable in some cases.

In preparing the modified lipopolysaccharides of this invention, it is deemed highly important that LPS can be deacylated at position 3 without causing any changes in the O-antigen or core regions or in the structure of the lipid A component except for loss of the labile fatty acyl residue. There are several implications of this result with respect to possible uses of the de-3-O-acylated compounds. For example, vaccines against gram negative bacteria and/or endotoxin can be generated using LPS that has been treated in the manner of this disclosure which results in a preparation with low endotoxicity but with the same antigenic attributes as the parent material, and which is able to act as its own adjuvant. Such preparations may be able to promote a strong specific immune response without the toxic effects generally associated with LPS-based vaccines.

Another implication is that lipid A that has been detoxified by de-3-O-acylation, since it still contains both phosphates, may have greater immunostimulatory activities than lipid A that has been detoxified by the prior art method involving acid hydrolysis to remove the reducing end phosphate. For example, acid hydrolyzed LPS, which is referred to as monophosphoryl lipid A (MPL), is less mitogenic with respect to B-lymphocyte proliferation than is d3-LPS. Thus, de-3-O-acylated lipid A and LPS may be more potent immunostimulators than is MPL. Furthermore, because of structural differences between MPL and de-3-O-acylated lipid A and LPS, the latter compounds may exhibit a different spectrum of beneficial biological activities than does MPL.

It is therefore viewed as a significant advance to be able to reduce the endotoxicity of LPS without eliminating its antigenic attributes or its immunostimulating activity. LPS subjected to mild alkaline hydrolysis can be used to immunize warm blooded animals including humans, thus conferring protection against gram-negative septicemia and associated endotoxemia.

A further advantage of d3-LPS and d3-DPL relative to MPL is that these materials, since they possess both of the phosphate groups present in lipid A, may exhibit enhanced activities relative to MPL, which is lacking the phosphate moiety at the 1 position. This has already been found with respect to mitogenicity; d3-LPS is as mitogenic as the parent LPS, whereas MPL is only about half as mitogenic.

Finally, the conditions used to effect the mild alkaline hydrolysis disclosed herein are, in some cases, easier to attain than those of the prior art methods for detoxifying LPS or lipid A. For example, as mentioned above, lipid A can be detoxified by dissolving it in a solution chloroform:methanol 2:1 (v/v), saturating this solution with an aqueous buffer consisting of 0.5M $Na_2CO_3$ at pH 10.5, and then evaporating the solvent at 45°–50° C. This method is also effective in removing the residual endotoxicity which is usually found in crude preparations of MPL, and which is typically removed by chromatographic purification. Thus, milk alkaline hydrolysis can obviate the need for the costly and time-consuming chromatography steps which are generally required in order to fully-detoxify preparations of MPL.

The lipopolysaccharide which is free of the $\beta$-hydroxymyristic acid residue, can be covered from the reaction medium in relatively pure form.

Although the present invention is particularly useful for de-3-O-acylating MPL, it is applicable to lipopolysaccharides in general. Lipopolysaccharides represent a biologically active class of substances and chemically are made up of a polysaccharide portion, the O-specific chains (O-antigen) and the core, and a covalently bound lipid, lipid A. Lipid A represents the endotoxically active region of lipopolysaccharides, while the polar polysaccharide part serves as a solubilizing carrier. Lipid A of Salmonella consists of a backbone of β-1,6-linked D-glucosamine disaccharide units which are substituted at positions 1 and 4' by phosphate-residues and at position 6' by the core polysaccharide. The other hydroxyl and the amino groups of the backbone are acylated by long-chain fatty acids, of which lauric, myristic, palmitic and 3-hydroxymyristic acid predominate.

The term "monophosphoryl lipid A", "(MPL)" or "(MLA)" as used herein is meant to designate the monophosphoryl lipid A of structure I and is obtained from lipopolysaccharides such as *Salmonella minnesota* R 595, *Escherichia coli*, and the like. MLA is reported by N. Qureshi et al. Journal of Biological Chemistry, Vol 260, No. 9. pages 5271–5278 (1985).

Accordingly, the lipopolysaccharide compounds of this invention after de-3-O-acylation, can also be represented by the formula.

A lipopolysaccharide compound of the formula

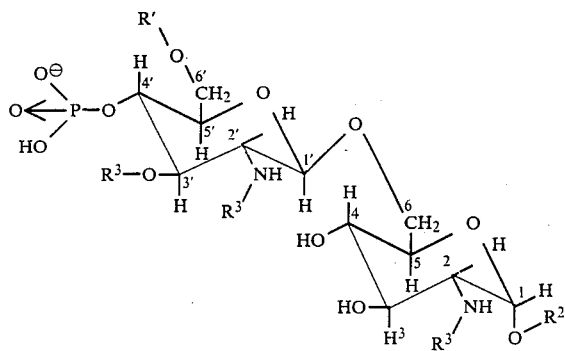

wherein $R^1$ is selected from the group consisting of hydrogen and the core component of enterobacterial lipopolysaccharide, with or without the O-antigen present, $R^2$ is selected from the groups H and $PO_3H_2$, and a $R^3$ is selected from the group consisting of H, β-hydroxymyristoyl, and a 3-acyloxyacyl residue having the formula:

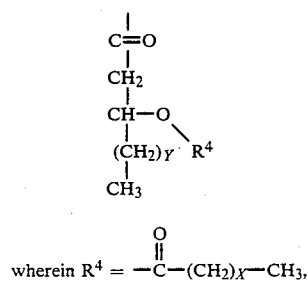

wherein $R^4 = -\overset{O}{\underset{\|}{C}}-(CH_2)_x-CH_3$, and wherein X and Y can have a value of from 0 up to about 20 and preferably 10, 12 or 14.

The compounds prepared by the present invention are therefore substantially pure compounds and not mixtures of partially de-O-acylated compounds.

All of the uses that are disclosed in the literature for MPL can be entertained with respect to d3-MPL and, especially, d3-DPL. Thse include (a) use as an adjuvant, (b) protection against radiation, (c) protection against gram negative septicemia and associated endotoxemia, (d) protection against non-specific infectious challenges, and (e) treatment of neoplastic disease. The de-3-O-acylated materials are used in the same way as MPL in all of these applications, i.e., at the same doses, in the same combinations.

Additionally, d3-LPS can be used as a vaccine against gram-negative infections. In this regard, the material is prepared from LPS obtained from either a wild-type strain of a gram negative organism or else from a strain that has a partially-complete (and therefore antigenically cross-reactive) core region (e.g. *E. coli* J5). Such d3-LPS can be administered either in saline, in a lipid emulsion system, or in an oil-in-water emulsion (1–2% squalane or squalene, 0.2% Tween 80). In the latter case, other bacterially-derived immunostimulants (CWS, TDM) can be used in combination with D3-LPS. The amount of d3-LPS per dose is between about 10 and about 1000 μg, and preferably between about 20 and about 200 μg. CWS and TDM, if used, and at similar levels per dose.

The following examples are illustrative of the present invention.

EXAMPLE 1

Removal of the β-Hydroxymyristic Acid at Position 3 of *Escherichia coli* D31M4 MPL by Treatment with Organic Alkaline Media 580 mg of crude *E. coli* D31m4 MPL was dissolved in 250 mls of chloroform:methanol 2:1 (v/v). This solution was transferred to a 1 liter separatory funnel, where it was washed with 100 mls 0.5M $Na_2CO_3$, pH 10.5. The organic phase was removed, and the solvent was stripped off by flash evaporation using a water aspirator and a bath temperature of 45° C. The resulting residue contained 615.9 mg of de-3-O-acylated MPL (d3-MPL), as judged by thin layer chromatography (Silica gel 60, chloroform:methanol:water:ammonium hydroxide 50:31:6:2 (v/v); plates visualized by spraying with ammonium molybdate in ethanol (10% w/v) and charring).

EXAMPLE 2

The 50% Lethal Dose in Chick Embryos ($CELD_{50}$ of Crude MPL Before and After De-3-O-Acylation MPL and d3-MPL (prepared in Example 1, above) were dispersed in sterile water containing 0.2% triethylamine (TEA; v/v) to a concentration of 2.0 mg/ml. An ultrasonic bath and mild warming (45°–50° C.) promoted solubilization. To these solutions were added equal volumes of 1.8% NaCl (w/v), giving final solutions that contained 1.0 ug/ml MPL or d3-MPL, 0.9% NaCl (w/v), and 0.1% TEA (v/v). The toxicity of these solutions in 11 day-old chick embryos was then assessed by the method of Milner and Finklestein (J. Infect. Diseases 116, 259: 1966). The chick embryo 50% lethal doses ($CELD_{50}$) were calculated by the method of Reed and Muench (Am. J. Hyg. 27, 493: 1938). The $CELD_{50}$ of the crude MPL used in Example 1 was found to be less than 1 μg. On the other hand, the d3-MPL did not kill any chick embryos even at 20 μg, the highest dilution tested.

EXAMPLE 3

De-3-O-Acylation of *Salmonella minnesota* R595 LPS by Treatment with Aqueous TEA Into a 4 ml screw-top vial was placed 10.1 mg *S. minnesota* R595 LPS. 2.0 ml sterile water was added to the vial, which was then capped and sonicated for 3 min. at room temperature. The vial was then placed in a boiling water bath. After 5 min. the vial was removed from the bath and 67 ul TEA was added to the solution, with stirring. The vial was capped and allowed to stand at room temperature for 43 hr. At this time, the extent of de-3-O-acylation was assessed by first subjecting a small portion of the reaction solution to acid hydrolysis, in order to convert all of the LPS to MPL. This was accomplished by adding 0.3 ml of 0.47N HCl to a 0.2 ml aliquot of the reaction solution, then placing the acidified solution into an oil bath (130° C.) for 10 min. The solution was stirred during this time. The solution was then cooled in an ice-water bath, and the MPL was extracted using 1.0 ml of chloroform:methanol 2:1 (CM 2:1; v/v). A control solution was prepared by dispersing 1.00 mg LPS in 0.2 ml water plus 6.7 ul TEA, adding 0.3 ml of 0.47N HCl, incubating in a 130° C. oil bath for 10 min., cooling and extracting with CM 2:1. The alkaline-hydrolyzed material and the control were then analyzed by TLC, as described in Example 1. TLC revealed that almost all of the MPL from the TEA-treated LPS was de-3-O-acylated, which indicated that the TEA treatment had resulted in the production of d3-LPS. The control sample, which had not been exposed TEA for the extended period, appeared identical to MPL from untreated LPS. The TEA hydrolysis reaction was therefore judged to be complete. The remaining reaction mixture was dialyzed against distilled water (6,000–8,000 MWt cutoff) and lyophilized, yielding 8.45 mg d3-LPS.

EXAMPLE 4

Biological Activity of d3-LPS

The endotoxicity of the d3-LPS prepared in example 3 was compared with that of the starting LPS using the $CELD_{50}$ assay, as described in Example 2. The activities of LPS and d3-LPS were also evaluated in a lymphocyte proliferation assay, based on uptake of $^3H$-thymidine by murine spleen cells following exposure to these materials. The results from these assays are shown in Table 1. They indicate that d3-LPS, while much less endotoxic than the parent LPS, is still a potent mitogen.

TABLE 1

The effect of de-3-0-acylation on the biological activities of S. minnesota R595 LPS.

| Sample | $CELD_{50}{}^a$ | Mitogenicity[b] C3H/FeJ[c] | CeH/HeJ[c] |
|---|---|---|---|
| LPS | 0.03 μg | 33.9 | 4.4 |
| d3-LPS | 1.4 μg | 30.0 | 5.2 |

Notes:
[a]The dose necessary to cause 50% mortality in 11 day old chick embryos.
[b]Lymphocyte proliferation assay, based on uptake of $^3H$-thymidine by murine spleen cells. The numbers represent the ratio of $^3H$ counts in stimulated cells to counts in unstimulated cells.
[c]C3H/FeJ mice are LPS-responsive; C3H/HeJ mice are LPS-unresponsive.

EXAMPLE 5

The Rate of De-3-O-Acylation and Detoxification of S. minnesota R595 Diphosphoryl Lipid A (DPL) in Organic Alkaline Media Into each of 4 100×16 mm test tubes was placed 2.0 mg S. minnesota R595 DPL. To each tube was added 5 ml CM 2:1 and 2 ml 0.5M $Na_2CO_3$ pH 10.5. The test tubes were vortexed, centrifuged for 5 min at 3000 g, and the organic layers were withdrawn and transferred to clean test tubes. These solutions were then incubated for varying periods of time at 51°–52° C. (0, 2, 5, and 10 min). The reactions were quenched at the indicated times by placing the tubes in an ice-water bath and adding ice chips to the solutions. After about 30 sec, 2.0 ml of 0.1N HCl was added to each test tube, and the tubes were vortexed and centrifuged. The organic layers were transferred to clean test tubes and washed with distilled water (plus ice chips). Finally, the organic layers were evaporated under a stream of nitrogen. A 0.4 mg portion of each residue was subjected to acid hydrolysis by the method described in Example 3, in order to convert the residues to the corresponding MPLs. The MPLs were then analyzed by TLC as described in Example 1, and the endotoxicities of the corresponding DPL residues from each time point were measured with the $CELD_{50}$ assay, as described in Example 2. The results are summarized in Table II.

TABLE II

The Rate of De-3-0-Acylation and Detoxification of S. minnesota R595 Diphosphoryl Lipid A (DPL) in Organic Alkaline Media.

| Incubation Time[a] | Extent of De-3-0-Acylation[b] | $CELD_{50}{}^c$ |
|---|---|---|
| 0 min | None | 0.085 μg |
| 2 | Half | NT |
| 5 | Almost complete | 1.78 |
| 10 | Complete | 10 μg |

Notes:
[a]The time each tube was incubated at 51–52° C.
[b]As judged visually from the TLC appearance of the MPL corresponding to the DPL at each time point.
[c]The dose necessary to cause 50% mortality in 11 day-old chick embryos.

Although the invention has been illustrated by the preceding examples, it is not to be construed as being limited to the materials employed therein but rather, the invention relates to the generic area as herein before disclosed. Various modifications and embodiments thereof can be made without departing from the spirit or scope thereof.

What is claimed is:

1. A method for modifying a lipopolysaccharide to selectively remove only the β-hydroxymyristic acyl residue that is ester-linked to the reducing-end glucosamine at position 3 of said lipopolysaccharide, which comprises subjecting said lipopolysaccharide to alkaline hydrolysis sufficient only to remove β-hydroxymyristic acid from position 3 without removal of other fatty acids from the lipopolysaccharide molecule and recovering said lipopolysaccharide free of said residue.

2. The method of claim 1 wherein said lipopolysaccharide is enterobacterial lipopolysaccharide.

3. The method of claim 1 wherein said lipopolysaccharide is monophosphoryl lipid A.

4. The method of claim 1 wherein said lipopolysaccharide is diphosphoryl lipid A.

5. The method of claim 1 wherein said hydrolysis is conducted in the presence of sodium carbonate.

6. The method of claim 1 wherein said hydrolysis is conducted in the presence of triethylamine.

7. The method of claim 1 wherein said hydrolysis is conducted in an organic medium.

8. The method of claim 1 wherein said hydrolysis is conducted in an aqueous medium.

9. The method of claim 1 wherein said hydrolysis is conducted at a pH of from about 10 to about 14 and at a temperature of from about 20° to about 80° C.

10. A method for removing from lipid A or monophosphoryl lipid A, only the β-hydroxymyristic acyl residue that is ester-linked to the reducing-end glucosamine at position 3 of said lipid A, which method comprises the steps of:
(a) dissolving said lipid A in an inert organic solvent;
(b) saturating said solvent with an aqueous buffer comprised of an alkaline compound, at a pH of from about 10 to about 13;
(c) flash evaporating said solvent under a vacuum at a temperature of between about 40° C. and about 60° C.; and
(d) recovering said lipid A.

11. The method of claim 10 wherein said lipid A is monophosphoryl lipid A.

12. The method of claim 10 wherein said inert, organic solvent is a mixture of chloroform and methanol.

13. The method of claim 10 which is effected in the presence of a phase transfer catalyst.

14. The method of claim 13 wherein said phase transfer catalyst is tetrabutyl ammonium bromide.

15. A lipopolysaccharide from which the β-hydroxymyristic acyl group has been removed from position 3.

16. An essentially pure lipopolysaccharide compound of the formula:

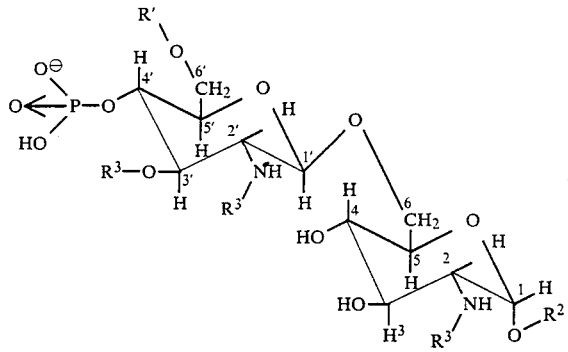

wherein $R^1$ is selected from the group consisting of hydrogen and the core component of enterobacterial lipopolysaccharide, with the O-antigen present, $R^2$ is selected from the groups H and $PO_3H_2$, and $R^3$ is selected from the group consisting of H, β-hydroxymyristoyl, and a 3-acyloxyacyl residue having the formula:

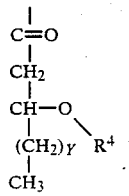

III wherein $R^4 = -\overset{O}{\underset{\|}{C}}-(CH_2)_X-CH_3$, and wherein X and Y have a value of from 0 up to about 20.

17. The compound of claim 16 wherein $R^1$ and $R^2$ are hydrogen.

18. The compound of claim 16 wherein $R^1$ is hydrogen and $R^2$ is $PO_3H_2$.

19. The compound of claim 16 wherein $R^1$ is the core component of enterobacterial lipopolysaccharide and $R^2$ is $PO_3H_2$.

20. The compound of claim 16 wherein $R^1$ and $R^2$ are hydrogen, and $R^3$ is the residue of Formula III.

21. The compound of claim 20 wherein X has a value of 10, 12 or 14 and Y is 10.

22. An essentially pure lipopolysaccharide compound of the formula:

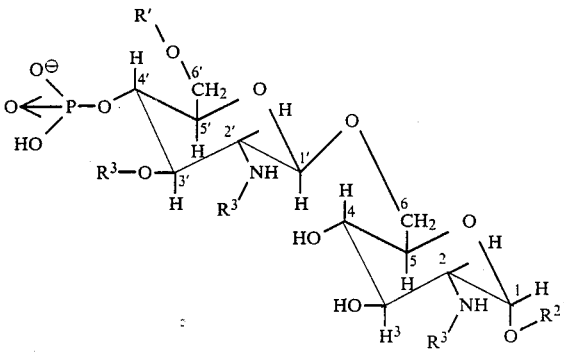

wherein $R^1$ is selected from the group consisting of hydrogen and the core component of enterobacterial lipopolysaccharide, without the O-antigen present, $R^2$ is selected from the groups H and $PO_3H_2$, and $R^3$ is selected from the group consisting of H, β-hydroxymyristoyl, and a 3-acyloxyacyl residue having the formula:

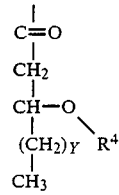

(III)

wherein $R^4 = -\overset{O}{\underset{\|}{C}}-(CH_2)_X-CH_3$, and wherein X and Y have a value of from 0 up to about 20.

23. A pharmaceutical composition comprising a substantially pure, modified lipopolysaccharide, having no β-hydroxymyristic acyl residue that is ester-linked to the reducing-end glucosamine at position 3, and a pharmaceutically acceptable carrier.

24. The pharmaceutical composition of claim 23 wherein said lipopolysaccharide is enterobacterial lipopolysaccharide.

25. The pharmaceutical composition of claim 23 wherein said lipopolysaccharide is monophosphoryl lipid A.

26. The pharmaceutical composition of claim 23 wherein said lipopolysaccharide is diphosphoryl lipid A.

* * * * *

UNITED STATES PATENT AND TRADEMARK OFFICE
CERTIFICATE OF CORRECTION

PATENT NO. : 4,912,094
DATED : February 15, 1994
INVENTOR(S) : Kent R. Myers and Alex T. Truchot It is certified that error appears in the above-identified patent and that said Letters Patent is hereby corrected as shown below:

<u>Title page,</u>
Item [75], Inventors, delete "Kent R. Meyers" and insert -- Kent R. Myers --.

<u>Column 2,</u>
Line 63, delete "*d-3-0-acyl*" and insert -- *de-3-0-acyl* --.

<u>Column 4,</u>
Line 14, delete "comprisinga" and insert -- comprising a--.

Signed and Sealed this

Twenty-ninth Day of April, 2003

JAMES E. ROGAN
*Director of the United States Patent and Trademark Office*

REEXAMINATION CERTIFICATE (2218th)
United States Patent [19]

Meyers et al.

[11] B1 4,912,094

[45] Certificate Issued   Feb. 15, 1994

[54] MODIFIED LIPOPOLYSACCHARIDES AND PROCESS OF PREPARATION

[75] Inventors: Kent R. Meyers; Alex T. Truchot, both of Hamilton, Mont.

[73] Assignee: Ribi Immunochem Research Inc., Hamilton, Mont.

Reexamination Request:
No. 90/002,766, Jun. 30, 1992

Reexamination Certificate for:
Patent No.: 4,912,094
Issued: Mar. 27, 1990
Appl. No.: 212,919
Filed: Jun. 29, 1988

[51] Int. Cl.$^5$ .................... C07H 1/00; C07H 13/02; C07G 17/00; C12P 19/04
[52] U.S. Cl. .................... 514/54; 536/124; 536/1.11; 536/119; 536/115; 536/117; 435/101
[58] Field of Search .............. 536/115, 117, 1.1, 124, 536/119, 1.11; 435/101; 514/54

[56] References Cited
U.S. PATENT DOCUMENTS 3,089,821  5/1963  Folkers ................. 514/54
4,029,762  6/1977  Galanos et al. .......... 530/387
4,185,090  1/1980  McIntire ............... 536/1.11

OTHER PUBLICATIONS

Qureshi et al., "Purification and Structural Determination of Nontoxic Lipid A Obtained from the Lipopolysaccharide of *Salmonella typhimurium*", J. Biol. Chem. 257, 11808–11815 (1982).

Qureshi et al., "Position of Ester Groups in the Lipid A Backbone of Lipopolysaccharides Obtained from *Salmonella typhimurium*", J. Biol. Chem. 258, 12947–12951 (1983).

Qureshi et al., "Application of Fast Atom Bombardment Mass Spectrometry and Nuclear Magnetic Resonance on the Structural Analysis of Purified Lipid A", J. Microbial. Meth. 5, 65–77 (1986).

Takayama et al., "Glucosamine-derived Phospholipids in *Escherichia coli* Structure and Chemical Modification of a Triacyl Glucosamine 1-Phosphate Found in a Phosphatidylglycerol-Deficient Mutant", J. Biol. Chem. 258, 14245–14252 (1983).

Takayama et al., "Separation and Characterization of Toxic and Nontoxic Forms of Lipid A", Rev. Infect. Dis. 6, 439–443 (1984).

Rietschel et al., "Concepts of the Chemical Structure of Lipid A", Rev. Infect. Dis. 6, 432–438 (1984).

Rietschel et al., "Chemical Structure and Biologic Activity of Bacterial and Synthetic Lipid A", Rev. Infect. Dis. 9, S527–S536 (1987).

Amano et al., "Structural Requirements of Endotoxic Glycolipid for Antitumor and Toxic Activity", J. Biochem. 93, 1391–1399 (1983).

Strain et al., "Characterization of Lipopolysaccharide from a Heptoseless Mutant of *Escherichia coli* by Carbon 13 Nuclear Magnetic Resonance", J. Biol. Chem. 258, 2906–2910 (1983).

Wollenweber et al., "Nature and Location of Amide-bound (R)-3-acyloxyacyl Groups in Lipid A of Lipopolysaccharides From Various Gram Negative Bacteria", Eur. J. Biochem. 145, 265–272 (1984).

Burhop et al., "Pulmonary Pressor Responses in Sheep to Chemically Defined Precursors of *E. coli* Endotoxin", J. Applied Physiology 62(3), 1141–1149 (1987).

Gould, Mechanism and Structure in Organic Chemistry, Holt, Rinehart and Winston, Inc., New York, 314–318 (1959).

Bligh et al., "A Rapid Method of Total Lipid Extraction and Purification", Can. J. Biochem. Physiol., 37, 911–917 (1959).

Ziegler et al., "Treatment of gram-negative bacteremia and shock with human antiserum to a mutant *Escherichia coli*", New England J. Med., 307(20):1225–1230 (1982).

Neter et al., "Studies of enterobacterial lipopolysaccharides: Effects of Heat and Chemicals on erythrocyte-modifying, antigenic, toxic and pyrogenic properties," J. Immunol., 76:377–385 (1956).

Niwa et al., "Alteration of physical, chemical, and biological properties of endotoxin by treatment with mild alkali," J. Bacteriol., 97(3):1069–1077 (1969).

Rietschel et al., "Nature and linkages of the fatty acids present in the Lipid-A component of Salmonella lipopolysaccharides," *Eur. J. Biochem.*, 28:166–173 (1972).

Goodman et al., "Mild alkaline hydrolysis of lipopolysaccharide endotoxin enhances its mitogenicity for murine B cells," *Infection and Immunity*, 17(1):205–214 (1977).

Amano et al., "Different structural requirements of endotoxic glycolipid for tumor regression and endotoxic activity," *Biochem. and Biophys. Res. Commun.*, 106(3):677–682 (1982).

Rosner et al., "Structure of lipopolysaccharide from an *Escherichia coli* heptose-less mutant," *J. Biol. Chem.*, 254(13):5906–5917 (1979).

Rietschel et al., "Lipid A, the endotoxic center of bacterial lipopolysaccharides: Relation of chemical structure to biological activity," in *Detection of Bacterial Endotoxins with the Limulus Amebocyte Lysate Test*, Alan R. Liss, pp. 25–53 (1987).

Qureshi et al., "Monophosphoryl Lipid A obtained from lipopolysaccharides of *Salmonella minnesota* R595," *J. Biol. Chem.*, 260(9):5271–5278 (1985).

Milner et al., "Bioassay of endotoxin: Correlation between pyrogenicity for rabbits and lethality for chick embryos," *J. Infect. Dis.*, 116(5):529–536 (1966).

Galanos et al., "Synthetic and natural *Escherichia coli* free Lipid A express identical endotoxic activities," *Eur. J. Biochem.*, 148:1–5 (1985).

Galanos et al., "Comparison of the capacity of two Lipid A precursor molecules to express the local Shwartzman phenomenon," *Infect. and Immun.*, 48(2):355–358 (1985).

Kotani et al., "Synthetic Lipid A with endotoxic and related biological activities comparable to those of a natural Lipid A from an *Escherichia coli* re-mutant", *Infect. and Immun.*, 49(1):225–237 (1985).

Galanos et al., "Biological activity of synthetic heptaacyl Lipid A representing a component of *Salmonella minnesota* R595 Lipid A," *Eur. J. Biochem.*, 160:55–59 (1986).

Kanegasaki et al., "Structure-activity relationship of Lipid A: Comparison of biological activities of natural and synthetic Lipid A's with different fatty acid compositions," *J. Biochem.*, 99:1203–1210 (1986).

Kotani et al., "Low endotoxic activities of synthetic Salmonella-type Lipid A with an additional acyloxyacyl group on the 2-amino group of $\beta$(1–6)glucosamine disaccharide 1,4'-bisphosphate," *Infect. and Immun.*, 52(3):872–884 (1986).

Rietschel et al., "Endotoxic properties of synthetic pentaacyl Lipid A precursor Ib and a structural isomer," *Eur. J. Biochem.*, 169:27–31 (1987).

Ribi et al., "Peptides as requirement for immunotherapy of the guinea-pig line-10 tumor with endotoxins," *Cancer Immunol. Immunother.*, 7:43–58 (1979).

Takayama et al., "Isolation of a nontoxic Lipid A fraction containing tumor regression activity," *Cancer Research*, 41:2654–2657 (1981).

Takayama et al., "Complete structure of Lipid A obtained from the lipopolysaccharides of the heptoseless mutant of *Salmonella typhimurium*," *J. Biol. Chem.*, 258(21):12801–12803 (1983).

Takayama et al., "Use of endotoxin in cancer immunotherapy and characterization of its nontoxic but active Lipid A components," in *Bacterial Lipopolysaccharides: Structure, Synthesis, and Biological Activity*, ACS Symposium No. 231, pp. 219–233 (1983).

Ribi, "Beneficial modification of the endotoxin molecule," *J. Biol. Resp. Mods.*, 3:1–9 (1984).

Ribi et al., "Lipid A and immunotherapy," *Rev. Infect. Diseases*, 6(4):567–572 (1984).

Nowortny, "Microbiology: Endotoxoid preparations," *Nature*, 197:721–722 (1963).

Johnson et al., "Relationship of structure to function in bacterial O antigens," *J. Bact.*, 87(4):809–814 (1964).

Nowotny, "Chemical detoxification of bacterial endotoxins," in *Bacterial Endotoxins*, Landy and Braun, eds., The State University, Rutgers, pp. 29–37 (1964).

Cundy et al., "Comparisons of five toxicity parameters of *Serratia marcescens* endotoxins," *Proc. Soc. Exp. Biol. Med.*, 127:999–1003 (1968).

Nowotny et al., "Relation of structure to function in bacterial O-antigens IV, fractionation of the components," *Ann. NY Acad. Sci.*, 133:586–603 (1966).

Tripodi et al., "Relation of structure to function in bacterial O-antigens V. nature of active sites in endotoxic lipopolysaccharides of *Serratia marcescens*," *Ann. NY Acad. Sci.*, 133:604–621 (1966).

Goodman et al., "Characterization of the chemical and physical properties of a novel B-lymphocyte activator, endotoxin protein," *Infection and Immunity*, 24(3):685–696 (1979).

Andersson et al., "The mitogenic effect of lipopolysaccharide on bone marrow–derived mouse lymphocytes," *J. Exp. Med.*, 137:943-953 (1973).

Raetz et al., "Molecular requirements for β-lymphocyte activation by *Escherichia coli* lipopolysaccharide," *Proc. Natl. Acad. Sci. USA*, 80:4624-4628 (1983).

Proctor et al., *Clin. Res.*, 31:498A (1984).

Takayama et al., "Influence of fine structure of Lipid A on Limulus amebocyte lysate clotting and toxic activities," *Infection and Immunity*, 45(2):350-355 (1984).

Wightman et al., "The activiation of protein kinase C by biologically active lipid moieties of lipopolysaccharide," *J. Biol. Chem.*, 259(16):10048-10052 (1984).

Takahashi et al., "Requirement of a Property Acylated (1-6)-D-blucosamine disaccharide structure for efficient . . . Lipid A," *Infect. and Immun.*, 65(1):57-68 (1987).

Ribi et al., "Preparation and antitumor activity of nontoxic Lipid A," *Cancer Immuno. Immunother.*, 12:91-96 (1982).

Somlyo et al., Int. J. Immunopharmac. 14, 131-142 (1992).

Kulshin et al., Eur. J. Biochem. 198, 697-401 (1991).

Takayama et al., Vaccine 9, 257-265 (1991).

Qureshi and Takayama, Molecular basis of bacterial pathogenesis (eds. Iglewski, B. H. and Clark, V. L.), Academic Press, San Diego, Calif., 1990, pp. 319-338.

Myers et al., "A critical determinant of Lipid A endotoxic activity", Cellular and Molecular Aspects of Endotoxin Reactions, eds. Nowotny, Spitzer and Ziegler, Elsevier, 1990, pp. 145-156.

Raetz et al., "Molecular Requirements for β-lymphocyte Activation by *Escherichia coli* Lipopolysaccharide", *Proc. Natl. Acad. Sci. USA*, vol. 80, pp. 4624-4628 Aug. 1983.

Wightman et al., "The Activation of Protein Kinase C by Biologically Active Lipid Moieties of Lipopolysaccharide," *The Journal of Biological Chemistry*, vol. 259, No. 16, Issue of Aug. 25, pp. 10048-10052 (1984).

Takayama et al., "Influence of Fine Structure of Lipid A on Limulus Amebocyte Lysate Clotting and Toxic Activities", *Infection and Immunity*, vol. 45, No. 2, pp. 350-355, Aug. 1984.

Matsura et al., "Biological Activities of Synthetic Lipid A Analogues," Bacterial Endotoxin, Weinheim, Deerfield Beach, Fla., pp. 81-72 (1984).

Rietschel et al., "Newer Aspects of the Chemical Structure and Biological Activity of Bacterial Endotoxin," *Progress in Clinical and Biological Research*, vol. 189, pp. 31-50 (1985).

Takada et al., "Structural Requirements of Lipid A for Endotoxicity and Other Biological Activities," *Critical Rev. Microbiol.*, vol. 16, pp. 477-523 (1989).

Takayama et al., "Complete Structure of Lipid A Obtained from the Lipopolysaccharides of the Heptoseless Mutant of *Salmonella typhimurium*," *J. Biol. Chem.*, vol. 258, pp. 12801-12803 (1983).

*Primary Examiner*—Ronald W. Griffin

[57] ABSTRACT

Modified lipopolysaccharides, particularly de-3-O-acylated monophosphoryl lipid A and de-3-O-acylated diphosphoryl lipid A, are provided by an alkaline hydrolysis under controlled conditions which removes only the β-hydroxymyristic acyl residue that is ester-linked to the reducing-end glucosamine at position 3. The modified products are less endotoxic and maintain the antigenic and immuno-stimulating properties.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–9, and 17–20 having been finally determined to be unpatentable, are cancelled.

Claims 10, 15, 16 and 21–26 are determined to be patentable as amended.

Claims 11–14 dependent on an amended claim, are determined to be patentable.

New claims 27–34 are added and determined to be patentable.

10. A method for *selectively* removing from *diphosphoryl* lipid A or monophosphoryl lipid A[,] only the β-hydroxymyristic acyl residue that is ester-linked to the reducing-end glucosamine at position 3 of said lipid A *to produce a de-3-O-acyl lipid A, wherein said de-3-O-acyl lipid A has reduced toxicity in comparison to the corresponding unmodified 3-O-acyl lipid A*, which method comprises the steps of:
  (a) dissolving said lipid A in an inert organic solvent;
  (b) saturating said solvent *containing said dissolved lipid A* with an aqueous buffer comprised of an alkaline compound, at a pH of from about 10 to about 13;
  (c) *separating the aqueous and organic phases and* flash evaporating [said solvent] *the organic phase* under a vacuum at a temperature of between about 40° C. and about 60° C.; and
  (d) recovering said [lipid A] *de-3-O-acyl lipid A*.

15. A [lipopolysaccharide from which the β-hydroxymyristic acyl group has been removed from position 3] *de-3-O-acyl diphosphoryl lipid A having reduced toxicity in comparison to the corresponding 3-O-acyl diphosphoryl lipid A*.

16. [An essentially pure] *A de-3-O-acyl lipopolysaccharide* [compound] *having reduced toxicity in comparison to the corresponding 3-O-acyl lipopolysaccharide* of the formula:

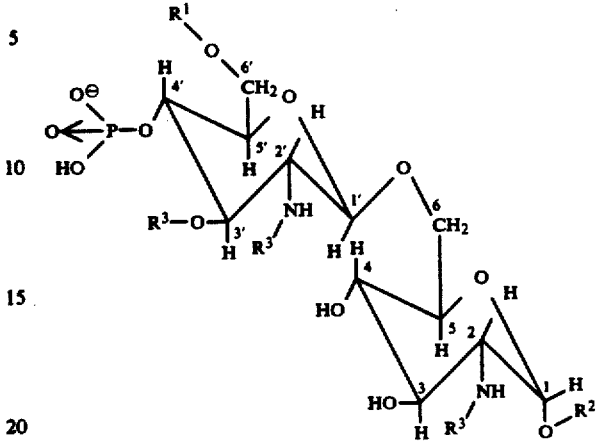

wherein:

$R^1$ is [selected from the group consisting of hydrogen and] the core component of enterobacterial lipopolysaccharide, with the O-antigen present, $R^2$ is [selected from the groups H and] $PO_3H_2$, and $R^3$ is selected from the group consisting of H, β-hydroxymyristoyl, and a 3-acyloxyacyl residue having the formula:

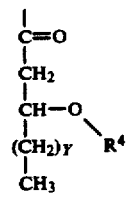

III wherein $R^4 = -\overset{O}{\underset{\|}{C}}-(CH_2)_x-CH_3$, and wherein X and Y have a value of from 0 up to about 20.

21. The compound of claim [20] *16*, wherein X has a value of 10, 12 or 14 and Y is 10.

22. [An essentially pure] *A d-3-O-acyl* lipopolysaccharide compound *having reduced toxicity in comparison to the corresponding 3-O-acyl lipopolysaccharide* of the formula:

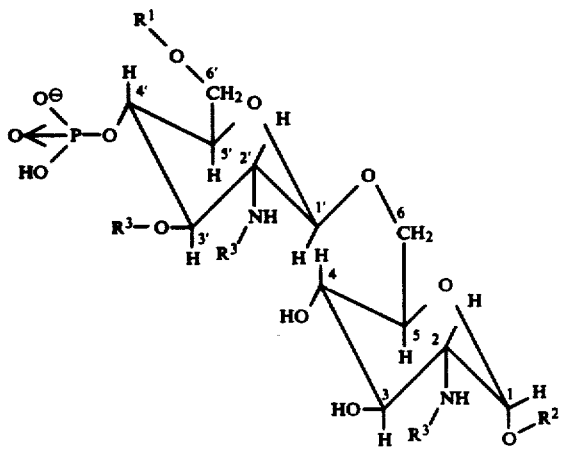

R¹ is [selected from the group consisting of hydrogen and] the core compound of enterobacterial lipopolysaccharide, without the O-antigen present, R² is [selected from the groups H and] $PO_3H_2$, and R³ is selected from the group consisting of H, β-hydroxymyristoyl, and a 3-acyloxyacyl residue having the formula:

III

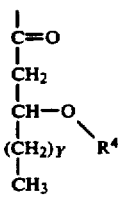

wherein $R^4 = -\overset{O}{\underset{\|}{C}}-(CH_2)_x-CH_3$, and wherein: X and Y have a value of from 0 up to about 20.

23. A pharmaceutical composition, comprising a substantially pure, modified lipopolysaccharide[, having no β-hydroxymyristic acyl residue that is ester-linked to the reducing-end glycocyamine at position 3], and a pharmaceutically acceptable carrier, wherein the modified lipopolysaccharide is a de-3-O-acyl lipopolysaccharide having reduced toxicity in comparison to the corresponding 3-O-acyl lipopolysaccharide.

24. The pharmaceutical composition of claim 23, wherein said *modified* lipopolysaccharide is enterobacterial *de-3-O-acyl* lipopolysaccharide.

25. The pharmaceutical composition of claim 23, wherein said *modified* lipopolysaccharide is *de-3-O-acyl* monophosphoryl lipid A.

26. The pharmaceutical composition of claim 23, wherein said *modified* lipopolysaccharide is *de-3-O-acyl* diphosphoryl lipid A.

27. A vaccine, protective against gram-negative bacteria and endotoxic components thereof, comprising a de-3-O-acyl lipopolysaccharide and a pharmaceutically acceptable carrier, wherein the lipopolysaccharide has a reduced toxicity in comparison to the corresponding 3-O-acyl lipopolysaccharide.

28. The vaccine of claim 27, wherein a single dose contains between about 10 μg and about 1000 μg of the lipopolysaccharide.

29. The vaccine of claim 28, wherein a single dose contains between about 20 μg and about 200 μg of the lipopolysaccharide.

30. De-3-O-acylated diphosphoryl lipid A produced by the method of claim 10.

31. De-3-O-acylated monophosphoryl lipid A produced by the method of claim 10.

32. A pharmaceutical composition comprising a substantially pure, modified lipopolysaccharide and a pharmaceutically acceptable carrier, wherein the modified lipopolysaccharide is a de-3-O-acyl enterobacterial lipopolysaccharide having reduced toxicity in comparison to the corresponding 3-O-acyl enterobacterial lipopolysaccharide.

33. A pharmaceutical composition, comprising a substantially pure, modified lipopolysaccharide and a pharmaceutically acceptable carrier, wherein the modified lipopolysaccharide is a de-3-O-acyl diphosphoryl lipid A having reduced toxicity in comparison to the corresponding 3-O-acyl diphosphoryl lipid A.

34. A pharmaceutical composition comprising a substantially pure, modified lipopolysaccharide and a pharmaceutically acceptable carrier, wherein the modified lipopolysaccharide is a de-3-O-acyl monophosphoryl lipid A having reduced toxicity in comparison to the corresponding 3-O-acyl monophosphoryl lipid A.

* * * * *